United States Patent
Thacker et al.

(10) Patent No.: US 7,801,621 B1
(45) Date of Patent: *Sep. 21, 2010

(54) NEURAL STIMULATION SYSTEM PROVIDING AUTO ADJUSTMENT OF STIMULUS OUTPUT AS A FUNCTION OF SENSED PRESSURE CHANGES

(75) Inventors: James R. Thacker, Eureka, MO (US); Carla Mann Woods, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 668 days.

This patent is subject to a terminal disclaimer.

(21) Appl. No.: 11/742,543

(22) Filed: Apr. 30, 2007

Related U.S. Application Data (63) Continuation of application No. 10/364,434, filed on Feb. 11, 2003, now Pat. No. 7,239,920.

(60) Provisional application No. 60/357,009, filed on Feb. 12, 2002.

(51) Int. Cl.
*A61N 1/00* (2006.01)
(52) U.S. Cl. .................. 607/62; 607/2; 607/46
(58) Field of Classification Search .......... 607/1, 607/2, 39–64
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,570,640 A | 2/1986 | Barsa | |
| 4,735,204 A | 4/1988 | Sussman et al. | |
| 4,911,174 A | 3/1990 | Pederson et al. | |
| 5,184,624 A | 2/1993 | Brown et al. | |
| 5,201,865 A | 4/1993 | Kuehn | |
| 5,333,618 A | 8/1994 | Lekhtman et al. | |

(Continued)

FOREIGN PATENT DOCUMENTS

WO   WO 97/09863   3/1997

(Continued)

OTHER PUBLICATIONS

Bradley et al, inventor for: U.S. Appl. No. 10/310,202, filed Dec. 3, 2001; entitled "Apparatus and Methods for Determining the Relative Position and Orientation of Neurostimulation Leads".

*Primary Examiner*—Scott M Getzow
(74) *Attorney, Agent, or Firm*—Vista IP Law Group LLP (57) ABSTRACT

A neural stimulation system automatically corrects or adjusts the stimulus magnitude in order to maintain a comfortable and effective stimulation therapy. Auto correction of the stimulus magnitude is linked to the measurement of pressure in the vicinity of the electrode-tissue interface. Because the pressure near the electrode-tissue interface can provide a measure of the electrode contacts' proximity to the neural tissue, and hence quantity of electrical energy delivered to the neural tissue, a change in the measured pressure or pressure morphology indicates that the stimulation energy may need to be adjusted. Hence, changes in pressure provide a feedback mechanism that permit the system to effectively auto correct the stimulus amplitude in order to maintain a desired therapeutic effect.

30 Claims, 6 Drawing Sheets

U.S. PATENT DOCUMENTS

| | | |
|---|---|---|
| 5,702,429 A | 12/1997 | King |
| 5,735,887 A | 4/1998 | Barreras, Sr. et al. |
| 5,758,651 A | 6/1998 | Nygard et al. |
| 5,814,092 A | 9/1998 | King |
| 5,895,416 A | 4/1999 | Barreras, Sr. et al. |
| 5,913,882 A | 6/1999 | King |
| 5,941,906 A | 8/1999 | Barreras, Sr. et al. |
| 6,027,456 A | 2/2000 | Feler et al. |
| 6,052,624 A | 4/2000 | Mann |
| 6,181,969 B1 | 1/2001 | Gord |
| 6,195,585 B1 | 2/2001 | Karunasiri et al. |
| 6,205,360 B1 | 3/2001 | Carter et al. |
| 6,353,762 B1 | 3/2002 | Baudino et al. |
| 6,381,496 B1 | 4/2002 | Meadows et al. |
| 6,393,325 B1 | 5/2002 | Mann et al. |
| 6,516,227 B1 | 2/2003 | Meadows et al. |
| 6,587,724 B2 | 7/2003 | Mann |
| 6,662,053 B2 | 12/2003 | Borkan |
| 6,735,475 B1 | 5/2004 | Whitehurst et al. |
| 6,751,505 B1 | 6/2004 | Van Den Honert et al. |
| 6,913,763 B2 | 7/2005 | Lerner |
| 6,993,384 B2 | 1/2006 | Bradley et al. |
| 2002/0022866 A1 | 2/2002 | Borkan |
| 2002/0143369 A1 | 10/2002 | Hill et al. |
| 2003/0139781 A1 | 7/2003 | Bradley et al. |
| 2004/0049235 A1 | 3/2004 | Deno et al. |
| 2004/0078067 A1 | 4/2004 | Thompson et al. |
| 2004/0082978 A1 | 4/2004 | Harrison et al. |
| 2004/0116978 A1 | 6/2004 | Bradley |
| 2004/0172083 A1 | 9/2004 | Penner |

FOREIGN PATENT DOCUMENTS

| | | |
|---|---|---|
| WO | WO 02/09808 | 2/2002 |

NEURAL STIMULATION SYSTEM PROVIDING AUTO ADJUSTMENT OF STIMULUS OUTPUT AS A FUNCTION OF SENSED PRESSURE CHANGES

This application is a continuation of U.S. application Ser. No. 10/364,434, filed Feb. 11, 2003 now U.S. Pat. No. 7,239,920, which claims the benefit of U.S. Application Ser. No. 60/357,009, filed Feb. 12, 2002, which application is herein incorporated by reference. This application is related to copending U.S. patent application Ser. No. 10/364,437, entitled "Neural Stimulation System Providing Auto Adjustment of Stimulus Output as a Function of Sensed Coupling Efficiency," and co-pending U.S. patent application Ser. No. 10/364,436, entitled "Neural Stimulation System Providing Auto Adjustment of Stimulus Output as a Function of Sensed Impedance," both filed Feb. 11, 2003. The entire disclosures of the above applications are expressly incorporated herein by reference.

BACKGROUND OF THE INVENTION

The present invention relates to neural stimulation systems and, more particularly, to an output control system that automatically maintains the output of the stimulation system at a comfortable and efficacious level.

The present invention may be used in various stimulation therapies in which a neurostimulator is used to stimulate neural tissue. One example where the present invention may be employed is with stimulation of peripheral nerves, e.g., the nerves in the arms, legs, fingers, which nerves are distant from the spinal cord. The present invention may also be used in stimulation of spinal cord nerves.

Spinal cord stimulation (SCS) systems, treat chronic pain by providing electrical stimulation pulses through the electrodes of an electrode array placed epidurally near a patient's spine. SCS is a well-accepted clinical method for reducing pain in certain populations of patients. SCS systems typically include an Implantable Pulse Generator (IPG) coupled to an array of electrodes at or near the distal end of an electrode lead. An electrode lead extension may also be used, if needed. The IPG generates electrical pulses that are delivered to neural tissue, e.g., the dorsal column fibers within the spinal cord, through the electrodes of the electrode array. In an SCS system, for example, the electrodes are implanted proximal to the dura mater of the spinal cord. Individual electrode contacts (the "electrodes") may be arranged in a desired pattern and spacing in order to create an electrode array. Individual wires, or electrode leads, connect with each electrode in the array. The electrode leads exit the spinal cord and attach to the IPG, either directly, or through one or more electrode lead extensions. The electrode lead extension, in turn, when used, is typically tunneled around the torso of the patient to a subcutaneous pocket where the IPG is implanted.

The electrical pulses generated by the SCS stimulation system, or other neural system, are also referred to as "stimulation pulses". In an SCS system, the stimulation pulses typically have the effect of producing a tingling sensation, also known as a paresthesia. The paresthesia helps block the chronic pain felt by the patient. The amplitude or magnitude of the stimulation pulses affects the intensity of the paresthesia felt by the patient. In general, it is desirable to have the amplitude of stimulation comfortably set to a level which produces paresthesia to block pain but not above a level that may actually result in pain apart from the native pain. Moreover, the stimulus amplitude should be set to a stimulus level lower than that which can recruit reflex motor nerves that can cause involuntary muscle contractions.

SCS and other stimulation systems are known in the art. For example, an implantable electronic stimulator is disclosed in U.S. Pat. No. 3,646,940 that provides timed sequenced electrical impulses to a plurality of electrodes. As another example, U.S. Pat. No. 3,724,467, teaches an electrode implant for neuro-stimulation of the spinal cord. A relatively thin and flexible strip of biocompatible material is provided as a carrier on which a plurality of electrodes are formed. The electrodes are connected by a conductor, e.g., a lead body, to an RF receiver, which is also implanted, and which is controlled by an external controller.

Representative techniques known in the art for providing for the automatic adjustment of stimulation parameters of an implantable stimulator are disclosed, e.g., in U.S. Pat. Nos. 5,895,416; 5,735,887; and 4,735,204.

Patients having an SCS system have heretofore had to manually adjust the amplitude of the stimulation pulses produced by their SCS system in order to maintain the paresthesia at a comfortable level. This is necessary for a number of reasons. For example, postural changes, lead array movement (acute and/or chronic), and scar tissue maturation, all affect the intensity of the paresthesia felt by the patient. Because of these changes, i.e., because of postural changes, lead array movement, and scar tissue maturation, as well as other changes that may occur in the patient, the paresthesia can be lost, or can be converted to painful over-stimulation, thereby forcing the patient to manually adjust the output. There is a need for a method or system that would eliminate, or at least mitigate, the need to perform such manual adjustments. Such method or system would be of great benefit to the patient.

SUMMARY OF THE INVENTION

In accordance with a first aspect of the present inventions, a method of stimulating neural tissue using at least one electrode is provided. The method comprises measuring pressure indicative of the electrical coupling efficiency between the electrode(s) and the neural tissue; for example, the relative pressure applied between the electrode(s) and the neural tissue. In one method, the pressure is measured in the vicinity of an interface between the electrode(s) and the neural tissue. The pressure can be measured in any region of a patient; for example, the epidural space. The method further comprises delivering stimulation energy through the electrode(s) to the neural tissue, and automatically adjusting the stimulation energy delivered through the electrode(s) to the neural tissue based on the pressure measurement.

In one method, a difference in the measured pressure is determined over time, in which case, the stimulation energy delivered through the electrode(s) to the neural tissue can be automatically adjusted based on the determined pressure difference. In another method, the magnitude of the stimulation energy delivered through the electrode(s) to the neural tissue is automatically adjusted based on the pressure measurement. For example, the magnitude of the stimulation energy can be automatically adjusted from one non-zero level to another different non-zero level. In still another method, one or more of a pulse amplitude, pulse width, and pulse frequency of the stimulation energy delivered through the electrode(s) to the neural tissue is automatically adjusted based on the pressure measurement.

The stimulation energy delivered through the electrode(s) to the neural tissue may be automatically adjusted for any purpose, but particularly lends itself well to the maintenance of an optimal level of therapy; for example, maintaining the stimulation energy in a predetermined therapeutic range of stimulation energy that elicits a response between a perception threshold and a discomfort threshold. In one method, the electrode(s) are mounted to an electrode lead, and the automatic adjustment of the stimulation energy is performed in an implantable pulse generator.

Another method may further comprise correlating a decrease or increase in the pressure measurement with an increase or decrease in stimulation energy delivered to the neural tissue, in which case, the stimulation energy delivered through the electrode(s) to the neural tissue may be automatically adjusted based on the correlation. The correlation step can be accomplished in any one of a variety of manners. For example, the correlation step may comprise linking each characteristic morphology caused by an event to a particular corrective adjustment for delivering a predetermined stimulation energy to the neural tissue, and storing the linked information between each characteristic morphology to a particular corrective adjustment. In this case, the method may further comprise recalling the linked information, wherein the stimulation energy delivered through the electrode(s) to the neural tissue can be automatically adjusted based on the recalled linked information. In one method, the event is a postural movement, in which case, the linking step may comprise measuring a pressure waveform for each postural movement while a patient makes various postural movements.

In accordance with a second aspect of the present inventions, a neural stimulation system is provided. The neural stimulation system comprises at least one electrode and a pressure transducer configured for detecting pressure indicative of the electrical coupling efficiency between the electrode (s) and the neural tissue; for example, the relative pressure applied between the electrode(s) and the neural tissue. In one embodiment, the pressure transducer is configured for detecting the pressure in the vicinity of an interface between the electrode(s) and the neural tissue. The pressure transducer can be configured for detecting pressure in any region of a patient; for example, the epidural space. The neural stimulation system further comprises analog circuitry configured for delivering stimulation energy to the electrode(s) in order to stimulate the neural tissue, and control circuitry configured for automatically adjusting the stimulation energy delivered from the analog circuitry to the electrode(s) based on the detected pressure. The neural stimulation system may comprise an electrode lead on which the electrode(s) is mounted, and an implantable pulse generator in which the analog circuitry and control circuitry are contained.

In one embodiment, the control circuitry can be configured for automatically adjusting the magnitude of the stimulation energy delivered to the electrode(s) based on the pressure detection. For example, the control circuitry may be configured for automatically adjusting the magnitude of the stimulation energy from one non-zero level to another different non-zero level. In another embodiment, the control circuitry can be configured for automatically adjusting one or more of a pulse amplitude, pulse width, and pulse frequency of the stimulation energy delivered to the at least one electrode based on the pressure detection. The control circuitry may be configured for automatically adjusting the stimulation energy delivered to the electrode(s) for any purpose, but particularly lends itself well to the maintenance of an optimal level of therapy; for example, maintaining the stimulation energy in a predetermined therapeutic range of stimulation energy that elicits a response between a perception threshold and a discomfort threshold. In still another embodiment, the control circuitry is configured for determining a difference in the measured pressure overtime, and for automatically adjusting the stimulation energy delivered to the electrode(s) based on the determined pressure difference.

In yet another embodiment, the neural stimulation system further comprises memory correlating a decrease or increase in the pressure measurement with an increase or decrease in stimulation energy delivered to the neural tissue, in which case, the control circuitry can be configured for automatically adjusting the stimulation energy delivered to the electrode(s) based on the correlation. The memory can provide this correlation function in any one of a variety of manners. For example, the memory may store information linking each characteristic morphology caused by an event to a particular corrective adjustment for delivering a predetermined stimulation energy to the neural tissue, in which case, the control circuitry can be configured for recalling the linked information from the memory and automatically adjusting the stimulation energy delivered to the electrode(s) based on the recalled linked information. In one embodiment, the event is a postural movement, in which case, the linking information may comprise a pressure waveform for each of a variety of postural movements.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 2:
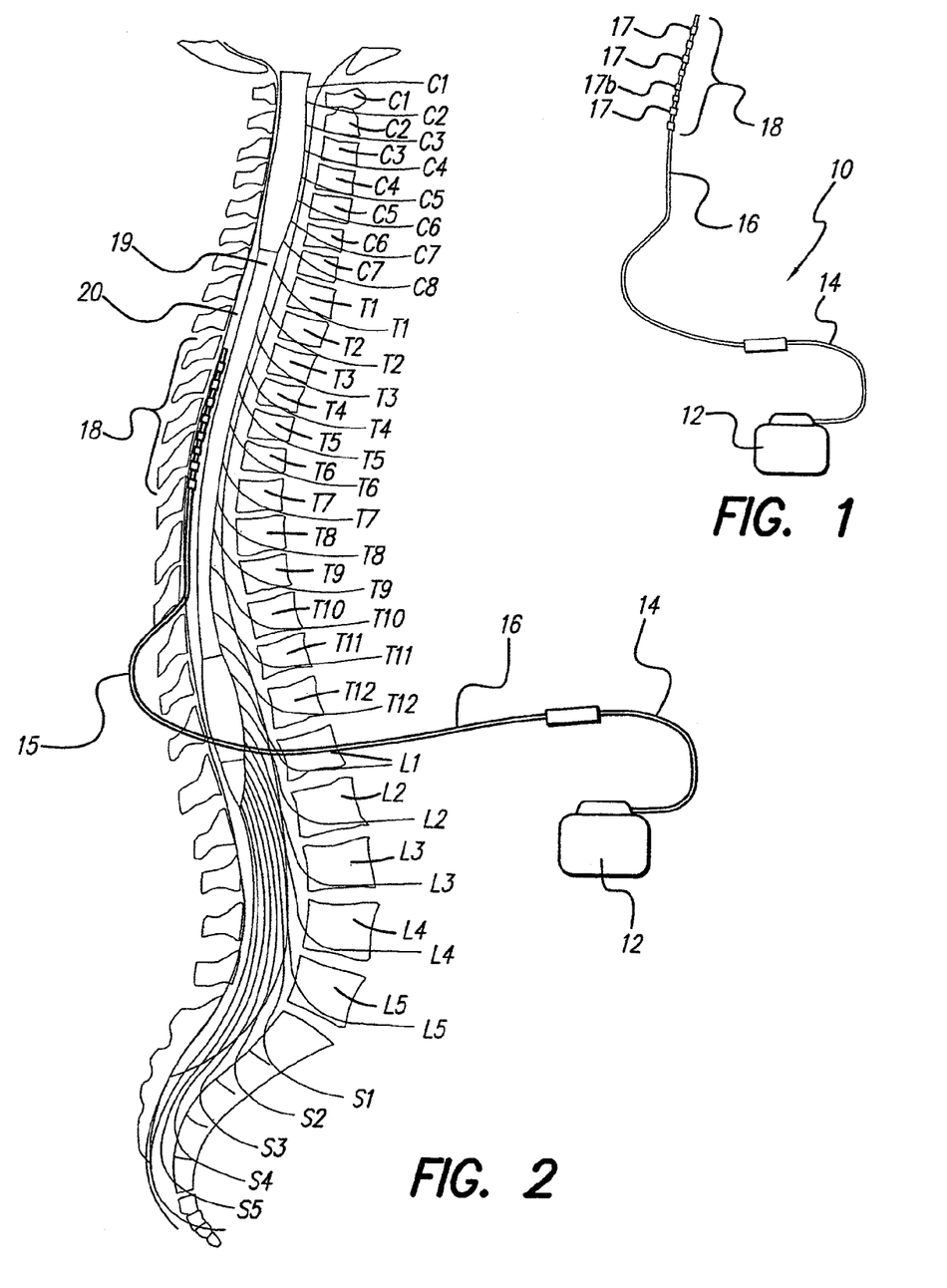
FIG. 1 shows a representative neural stimulation system of the type with which the present invention may be used.
FIG. 2 shows the stimulation system of FIG. 1 being used as a Spinal Cord Stimulation (SCS) system, with the electrode array inserted alongside the spinal cord in the epidural space, in close proximity to the dura mater.

A representative neural stimulation system 10 is shown in FIG. 1. Such system typically comprises an Implantable Pulse Generator (IPG) 12, a lead extension 14, an electrode lead 16, and an electrode array 18. The electrode array includes a plurality of electrode contacts 17 (also referred to as "electrodes"). The electrodes 17 are arranged, for example, in an in-line array 18 near the distal end of the lead 16. Other electrode array configurations may also be used. The IPG 12 generates stimulation current pulses that are applied to selected ones of the electrodes 17 within the electrode array 18. In accordance with the teachings of the present invention, a pressure transducer, or other pressure sensor, 17b, may be carried on the body of the lead 16 near the distal end of the lead.

A proximal end of the lead extension 14 is removably connected to the IPG 12, and a distal end of the lead extension 14 is removably connected to a proximal end of the electrode lead 16. The electrode array 18, is formed on a distal end of the electrode lead 16. The in-series combination of the lead extension 14 and electrode lead 16, carry the stimulation current from the IPG 12 to electrodes of the electrode array 18. It should be noted that the lead extension 14 need not always be used with the neural stimulation system 10. The lead extension 14 is only needed when the physical distance between the IPG 12 and the electrode array 18 requires its use.

Turning next to FIG. 2, the neural stimulation system 10 is shown being used as a Spinal Cord Stimulator (SCS) system. In such configuration, the lead 16, and more particularly the electrode array 18, including a pressure sensor that may be included as part of the array, is implanted in the epidural space 20 of a patient so as to be in close proximity to the spinal cord 19. Due to the lack of space near the lead exit point 15 where the electrode lead 16 exits the spinal column, the IPG 12 is generally implanted in the abdomen or above the buttocks. The lead extension 14 facilitates locating the IPG 12 away from the lead exit point 15.

A more complete description of an SCS system may be found in U.S. patent application Ser. No. 09/626,010, filed Jul. 26, 2000, now issued as U.S. Pat. No. 6,516,227, which patent is assigned to the same assignee as is the present application, and is incorporated herein by reference in its entirety.

Figure 3A:
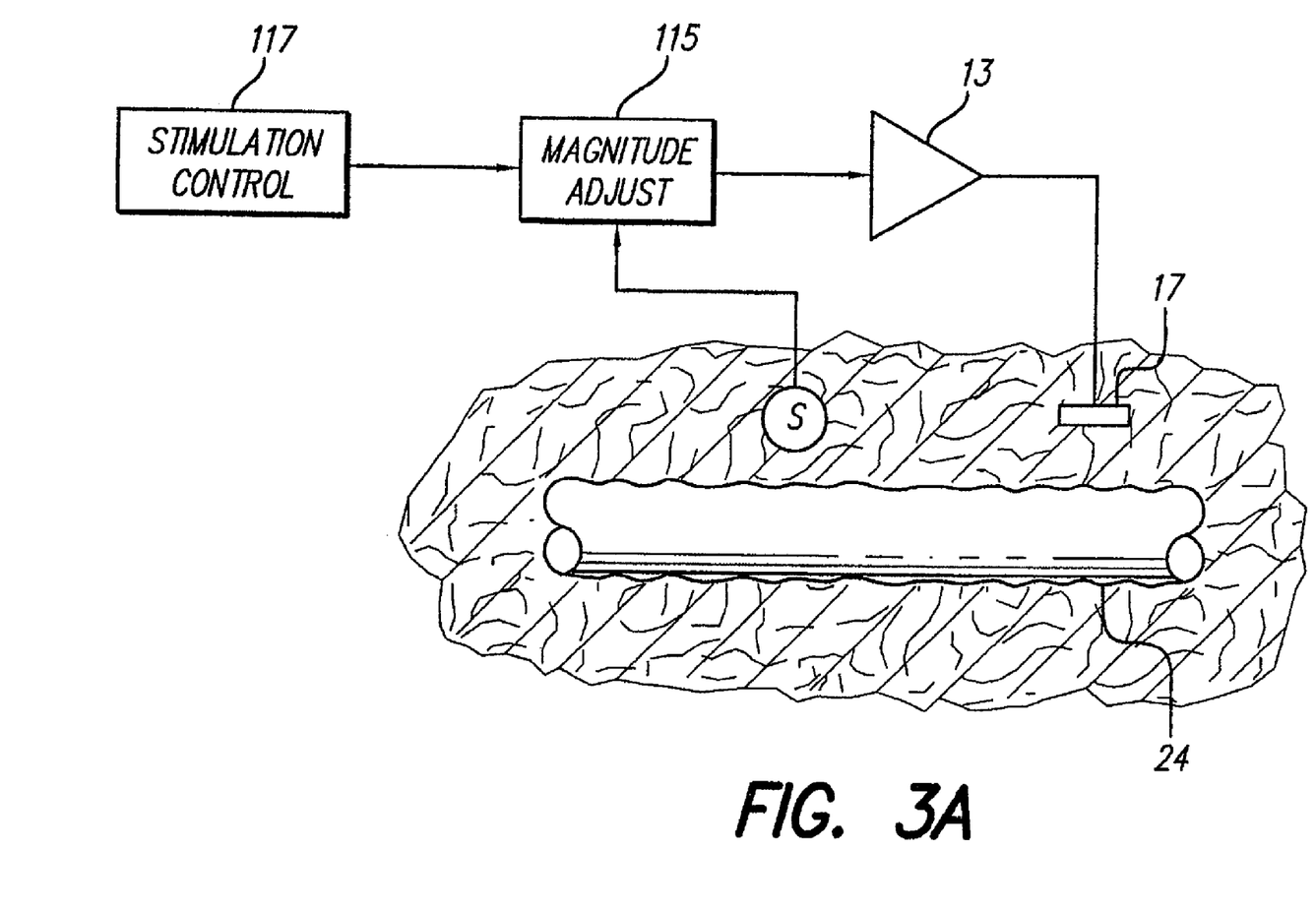
FIG. 3A is a block diagram of a system that automatically adjusts the amplitude of the stimulus current applied to neural tissue in accordance with the present invention.

Next, with respect to FIG. 3A, there is shown a functional block diagram of a system that automatically adjusts the amplitude of the stimulus current applied to neural tissue in accordance with the present invention. As seen in FIG. 3A, an electrode 17 is placed in close proximity to neural tissue 24 that is to be stimulated. The electrode 17 is electrically connected to a current pulse generator 13 which generates a stimulus pulse having a magnitude that is set by magnitude adjust circuitry 115. The magnitude adjust circuitry 115 sets the magnitude of the stimulus pulse as specified by stimulation control circuitry 117. The stimulation control circuitry 117 usually comprises some sort of processor, or state logic, that operates in accordance with a stored program or state diagram. It initially sets the magnitude of the stimulus pulse to a programmed or predetermined value.

As the stimulus pulse is applied to the neural tissue 24, an appropriate pressure sensor S senses the coupling efficiency between the stimulus current and the neural tissue. That is, the pressure sensor S provides a measure of how effective the applied stimulus is at stimulating the neural tissue 24. The sensor S is connected to the magnitude adjust circuitry 115 so as to provide a feedback signal that indicates whether the magnitude of the stimulus needs to be adjusted up or down. For example, should the pressure measurement with sensor S indicate that very little of the energy is being coupled to the neural tissue 24, then the feedback signal provided through the sensor S automatically causes the magnitude adjust circuitry 115 to increase the magnitude of the stimulus pulse so that the total stimulus energy delivered to the neural tissue 24 remains about the same. Conversely, should the pressure measurement with sensor S indicate that more energy is being coupled to the neural tissue 24, then the feedback signal provided through the sensor S automatically causes the magnitude adjust circuitry 115 to decrease the magnitude of the stimulus pulse so that the total energy delivered to the neural tissue 24 remains about the same. Thus, it is seen that the magnitude adjust circuitry 115 automatically adjusts the magnitude, e.g., amplitude, of the stimulus pulse so that the energy coupled to the neural tissue remains more or less the same. It may be appreciated that while stimulus energy is generally determined by adjusting stimulus amplitude while holding pulsewidth and the frequency of the stimulus pulses (pulses per second) constant, it is also possible to vary the stimulus energy by changing one or more of the stimulus parameters: pulse amplitude, pulsewidth and frequency.

In accordance with the present invention, coupling efficiency is determined by measuring the relative pressure changes in the vicinity of the electrode-tissue interface. Such relative pressure measurement can provide a quantitative measure of the stimulating electrode's positional relationship relative to the target neural tissue, which determines the coupling efficiency between the electrode and neural tissue. For example, as the relative pressure increases, that means the electrode contact may have moved closer to the neural tissue 24, thereby making the coupling efficiency higher. Conversely, as the relative pressure decreases, that means the electrode contact may have moved farther away from the neural tissue 24, thereby making the coupling efficiency lower. Thus, for purposes of the present invention, the sensor S measures relative pressure.

Figure 3B:
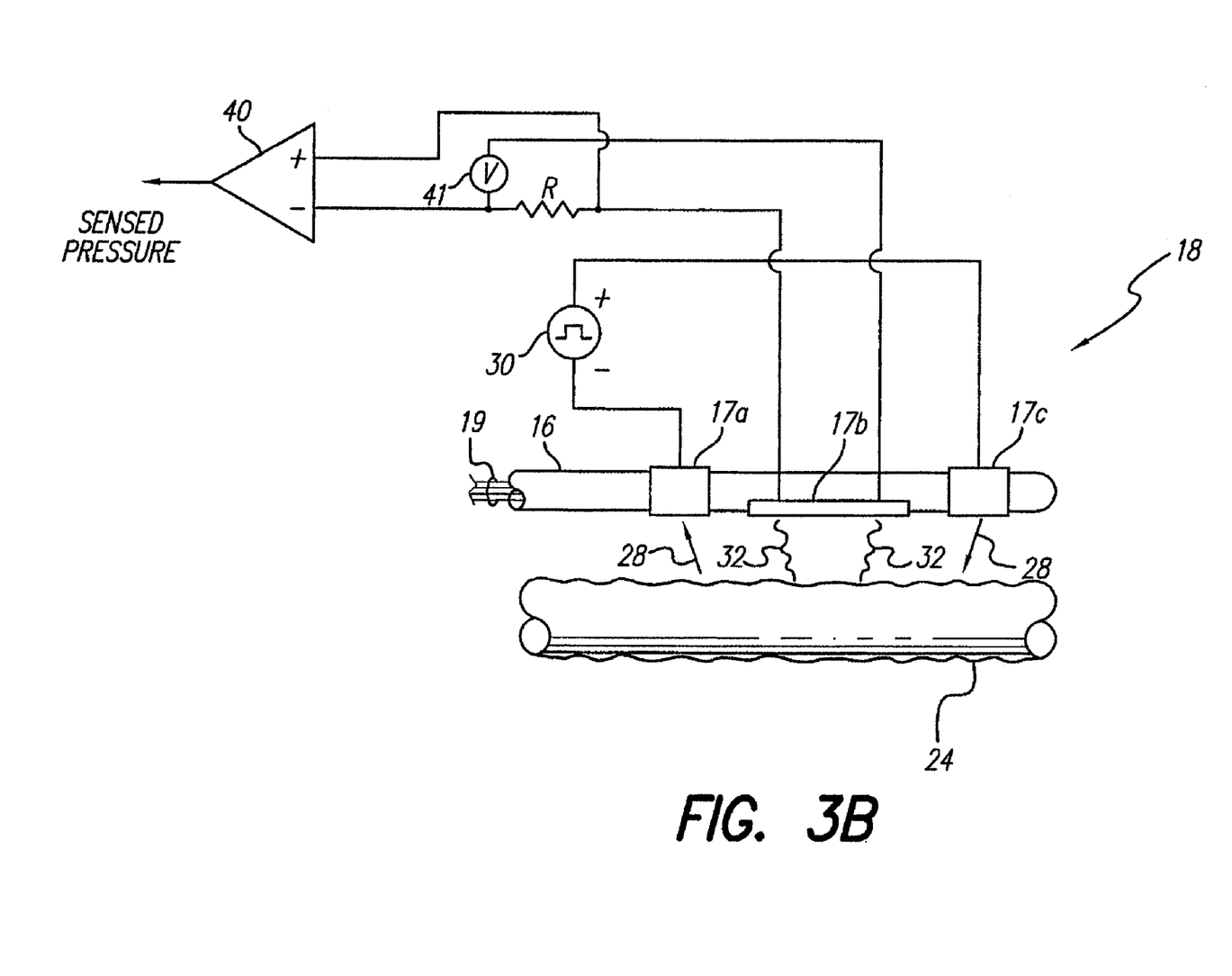
FIG. 3B illustrates one method for generating and sensing relative pressure in accordance with the invention.

Next, with respect to FIG. 3B, there is shown one method for measuring the relative pressure. Shown in FIG. 3B is a schematic representation of the distal end of the lead 16, including two electrode contacts 17a and 17c, and a suitable pressure transducer 17b. Lead 16 used with the neural stimulation system will have at least one electrode contact, and will usually have a plurality of electrode contacts, e.g., four, eight, sixteen or more electrode contacts. The two electrode contacts 17a and 17c shown in FIG. 3B is intended to be illustrative only, and not limiting. It is also to be understood that the physical and electrical connection with the electrode contacts 17a and 17c, and the pressure sensor 17b, is typically made through wires 19 that pass through the body of the lead 16. However, for simplicity of illustration in the schematic diagram of FIG. 3B, the electrical connections with the respective electrode contacts 17a, 17c and the pressure sensor 17c, are shown by wires external to the body of the lead 16. The electrode contacts 17a and 17c, as well as the pressure sensor 17b, are positioned in the epidural space near the dorsal column fibers 24 within or near the spinal cord.

In operation, a stimulation pulse, from a pulse generator 30, is applied to a selected pair of the electrode contacts, e.g., electrode contacts 17a and 17c. As connected in FIG. 3B, the polarity of the pulse generator 30 causes a current, represented by arrow 28, to be emitted from electrode contact 17c to the neural tissue 24. The current 28 flows through the nerve tissue 24 and surrounding tissue and returns to the pulse generator 30 through electrode contact 17a. The energy contained within the current 28 is coupled to the neural tissue 24 as a function of the coupling efficiency between electrode contacts 17a, 17c and the neural tissue 24. This coupling efficiency may vary, for many reasons, such as postural changes, relative movement between the lead 16 and tissue 24, or scar tissue maturation, to name just a few.

The electrode array 18 typically fits snugly within the epidural space next to the spinal column. There is thus a relative pressure applied against the electrode contacts 17a and 17c, as well as the pressure sensor 17b. This relative pressure generally provides information on the proximity of the electrode contacts 17a and 17c to the neural tissue 24, and thus also provides a relative quantitative measure of the electrode array's theoretical effectiveness in providing therapeutic stimulation. Such relative pressure is schematically represented in FIG. 3B by the wavy lines 32.

The relative pressure 32 may be sensed in various ways. One way is through a pressure transducer 17b. A typical pressure transducer is coupled to a voltage source 41 such that an electrical current flows through the transducer. As the relative pressure felt at the transducer changes, the impedance of the transducer changes, and thus the current that flows through the transducer changes. Hence, by monitoring changes in the current that flows through the transducer 17b, a measure is provided of the relative change in pressure felt at the transducer. One way in which the current flowing through the transducer 17b may be measured is by monitoring the voltage developed across a small resistance R connected in series with the transducer using a suitable amplifier 40, as shown in FIG. 3B. The voltage applied across the transducer 17b may be a pulsed voltage or a constant (dc) voltage. The output signal obtained from the amplifier 40 thus becomes a measure of the sensed relative pressure.

It is to be emphasized that the technique shown in FIG. 3B for sensing relative pressure is only representative of various ways that may be used. For example, a suitable piezoelectric element, carried on the distal end of the lead body, may be biased with an appropriate voltage and coupled to an oscillator circuit wherein the frequency of oscillation is a function of pressure felt by the transducer. Additionally, any suitable "strain gauge" can be fashioned so as to be carried on the body of the lead 16, and therefore provide a means for measuring the relative pressure sensed at the electrode array, and hence provide a means for measuring the coupling efficiency between the electrode contacts and the neural tissue.

Further, it should also be noted that the pressure sensor or transducer need not be carried by or on the lead body. Rather, a separate, dedicated pressure transducer may be used to monitor the relative pressure in the vicinity of the electrode array. Such separate transducer may be included on a separate lead.

Figure 4:
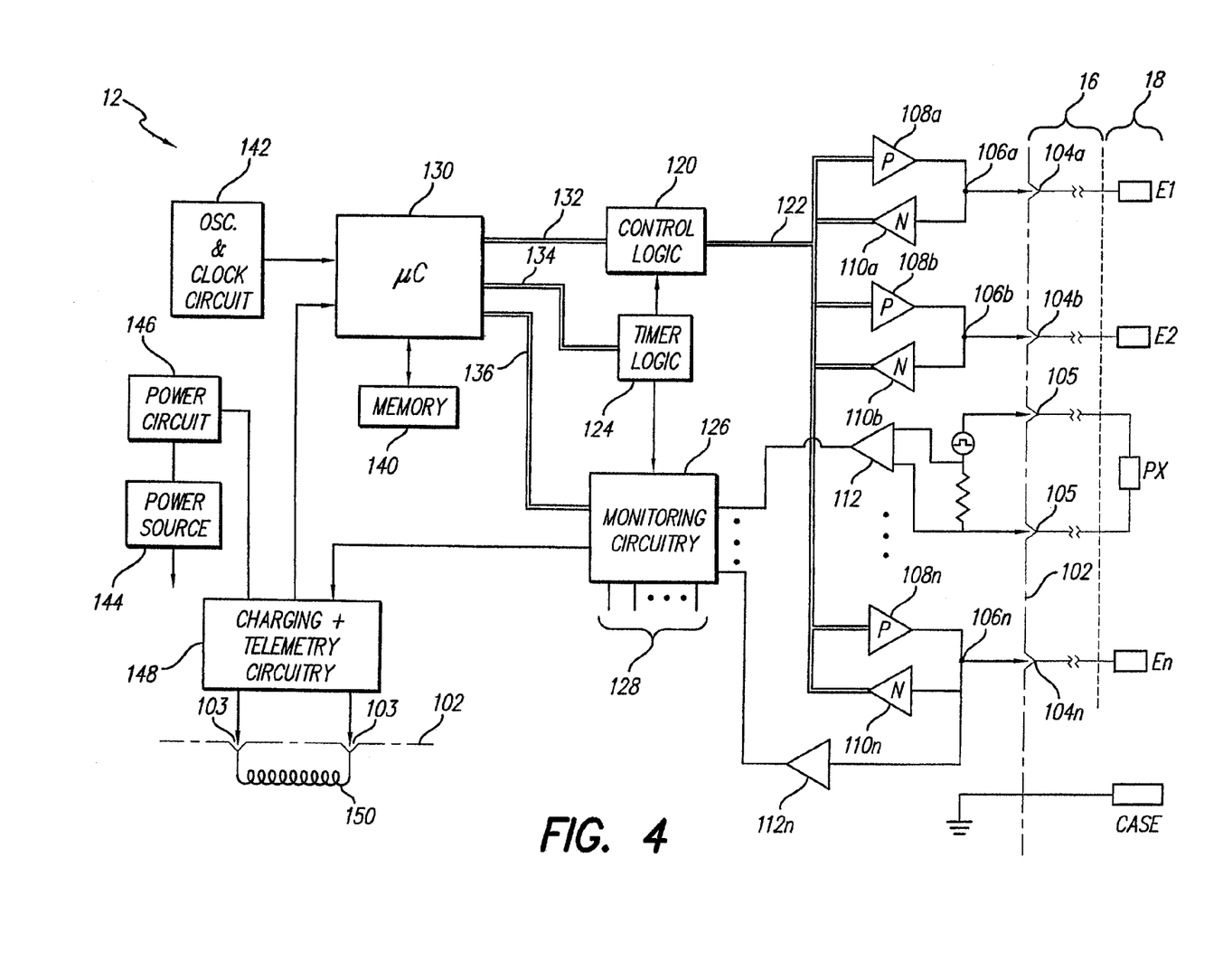
FIG. 4 is a block diagram of a representative Implantable Pulse Generator (IPG) that may be used to practice the present invention.

Turning next to FIG. 4, there is shown a functional block diagram of a representative Implantable Pulse Generator (IPG) 12 (or, with respect to FIG. 3, pulse generator 30) that may be used to practice the present invention. As seen in FIG. 4, the IPG 12 is connected to a multiplicity of electrode contacts E1, E2, . . . En, where n represents an integer of at least 2. The dotted-dashed line 102 in FIG. 4 represents the boundary between the outside of the IPG case (which is exposed to body tissues and fluids when the IPG is implanted) and the inside of the IPG case (which forms an hermetically sealed compartment wherein the electronic and other components are protected from the body tissues and fluids). Feed-through terminals 104a, 104b, . . . 104n are thus used to provide an electrical path through the IPG case wall 102. The feed-through terminals 104a, 104b, . . . are electrically connected to the electrodes E1, E2, . . . En through wires within the lead 16.

Thus, it is seen that each electrode contact E1, E2, . . . En is connected through a respective feed-through terminal 104a, 104b, . . . 104n to a respective circuit node 106a, 106b, . . . 106n within the hermetically sealed IPG case. This node, in turn is connected to a P-DAC circuit 108a and an N-DAC circuit 110a. Each of the other circuit nodes 106b, . . . 106n within the IPG similarly have a respective P-DAC circuit and N-DAC circuit connected thereto.

A pressure transducer PX is also connected through feed through terminals 105 to a suitable measuring circuit. For example, a pulsed voltage source 113 is used to apply a voltage potential across the transducer PX, and then the current flowing through the transducer PX is measured, e.g., as the voltage developed across a series resistance R, using a suitable amplifier 112. Other techniques and monitoring circuitry, both digital and/or analog, may also be used to perform this measuring function, and a wide variety of different types of pressure transducers may likewise be used.

A case electrode, CASE, may also be provided that effectively provides a common or return electrode that may be used with some stimulation and sensing configurations, as required.

In operation, in order to generate a stimulus current pulse that is applied between electrodes E1 and E2, for example, the P-DAC circuit 108a, as controlled by control logic 120 over data bus 122, causes a stimulation current having a specified amplitude to be emitted from the node 106a, and hence to be emitted from the electrode contact E1. At the same time, the N-DAC circuit 110b, similarly controlled by control logic 120, causes a stimulation current of the same magnitude to be received through node 106b, and hence through electrode contact E2. (Not shown in FIG. 4, but assumed to be present, are coupling capacitors connecting the respective nodes 106 and feed-through terminals 104.) In this way, a precisely controlled current is generated that flows from electrode contact E1 to electrode contact E2 through whatever body and nerve tissue resides between electrodes E1 and E2. The duration of the current flow, i.e., the width of the current pulse that is generated, is controlled by timer logic circuitry 124. The operation of this output circuitry, including alternative embodiments of suitable output circuitry for performing the same function of generating current stimulus pulses of a prescribed amplitude and width, is described more fully in the above-referenced U.S. patent application Ser. No. 09/626,010, now issued as U.S. Pat. No. 6,516,227.

The relative pressure is monitored through the pressure transducer PX. Such monitoring may be on a continuous or sampled basis. If sampled, the sampling is preferably done at a time other than the time when the stimulation pulse is applied to the selected electrodes. The sense amplifier 112 connects to monitoring circuitry 126. One or more additional sense amplifiers 112n may also monitor the voltage at various ones of the nodes 106a, 106b, 106n, to thereby provide a means for measuring the voltage at selected nodes. Such voltage measurement in conjunction with the known current flowing between selected electrodes provides a means for determining the impedance between the selected electrodes. The impedance measurement, in turn, provides an alternative measure of the coupling efficiency between the electrodes selected to perform the stimulation. The monitoring circuitry 126 also monitors other signals 128 from various locations or components within the IPG, e.g., battery voltage, charge current, etc.

The control logic 120, the timer logic 124, and the monitoring circuit 126 are controlled or watched by a suitable micro-controller (µC) circuit 130. The µC circuit 130 is coupled to the control logic 120, the timer logic 124, and the monitoring circuitry 126 over data buses 132, 134 and 136, respectively.

Suitable memory circuitry 140 is likewise coupled to the µC 130, as is an oscillator and clock circuit 142. The µC 130, in combination with the memory circuit 140 and oscillator and clock circuit 142, thus comprise a microprocessor system that carries out a program function in accordance with a suitable program stored in the memory 140. Alternatively, for some applications, the function provided by the microprocessor system may be carried out by a suitable state machine.

Power for the IPG is provided by way of a suitable power source 144, such as a rechargeable or primary battery. A power circuit 146 can be used to control the charging or replenishment of the power source, as described more fully in the above-referenced patent application Ser. No. 09/626,010, now issued as U.S. Pat. No. 6,516,227.

The power circuit 146, the µC 130 and the monitoring circuitry 126 are also coupled to charging and telemetry circuitry 148. An antenna coil 150 is likewise coupled to the telemetry circuitry 148. It is through the antenna coil 150 that charging, forward telemetry and back telemetry signals may be received and sent to an external device, such as an external programmer or charging circuit, as described more fully in the above-referenced patent application Ser. No. 09/626,010. In practice, separate coils may be used for charging, forward telemetry and back telemetry functions, as described more fully in the above-referenced U.S. Pat. No. 6,516,227, but for purposes of the present invention those distinctions are not important.

In FIG. 4, the antenna coil(s) 150 is shown as being outside the hermetically sealed case of the IPG. In such configuration, feed-through terminals 103 are used to allow the coil(s) to be electrically connected to the charging and telemetry circuitry 148, which are inside the hermetically sealed case. Alternatively, if the case is made from a non-ferromagnetic material, such as titanium, or ceramic, the coil(s) 150 may be located inside of the hermetically sealed case.

It is to be emphasized that the schematic illustration of FIG. 4 is intended to be functional, and not limiting. Those of skill in the art will be able to fashion appropriate circuitry, whether embodied in digital circuits, analog circuits, software and/or firmware, or combinations thereof, in order to accomplish the desired functions.

Figure 5:
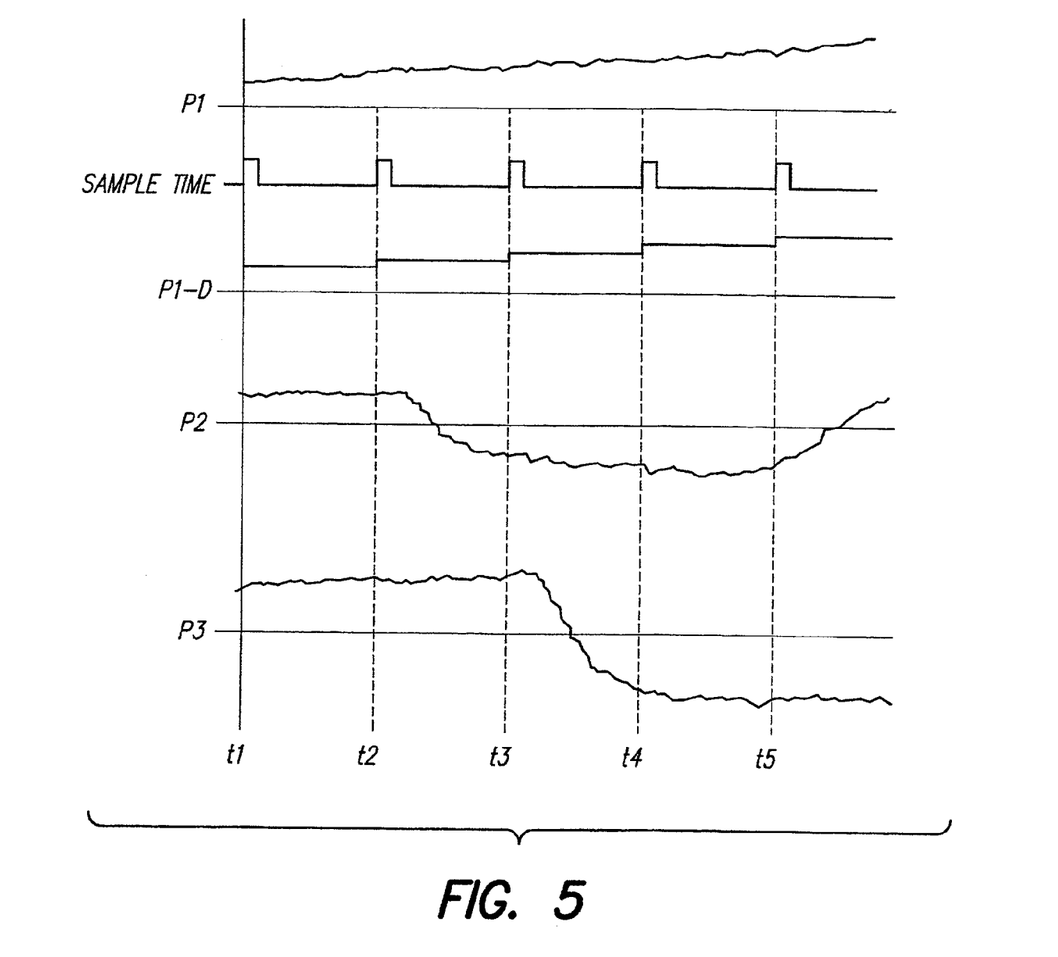
FIG. 5 is a timing waveform diagram that depicts various types of pressure measurements (P1, P1-D, P2, P3) that may be sensed as a function of time during operation of an SCS, or other neural stimulation, system.

FIG. 5 is a timing waveform diagram that depicts various types of representative pressure measurements (P1, P1-D, P2, P3) that may be sensed as a function of time. The measurements may be continuous or sampled. If sampled, a sampling pulse is generated at periodic intervals, and, e.g., the value of the pressure measurement P1 at the sample time is held as a fixed value until the next sample time, as represented by the waveform P1-D.

As seen in FIG. 5, at time t1, the three pressure measurements are all about the same value. At time t2, all three pressure measurements have increased slightly. The pressure measurement P1 continues to gradually increase through times t3, t4 and t5. Such gradual increase in the pressure measurement could be indicative of a slowly migrating lead.

In accordance with the present invention, and in response to sensing a slight increase in the relative pressure measurement P1 between times t1 through t5, the correction circuitry programmed or wired into the µC 130 can decrease the amplitude of the stimulation current by a small amount, thereby maintaining the stimulus energy delivered to the neural tissue at a predetermined, constant level or, alternatively, a predetermined level range. Had the relative pressure measurement P1 slightly decreased over the relevant time periods, then the amplitude of the stimulation current would have been increased a small amount.

As further seen in FIG. 5, shortly after time t2, the pressure measurement P2 drops quite rapidly and remains relatively low through times t3, t4 and t5. However, after time t5 the pressure returns to near its initial value. Such a sudden dip in the pressure measurement, with a return to its initial value, could be indicative of a temporary movement in the lead position caused, e.g., by a change in the patient's posture.

As additionally illustrated in FIG. 5, shortly after time t3, the pressure measurement P3 suddenly drops to a relatively low value, and remains low through times t4 and t5 and thereafter. Such a sudden permanent drop in the relative pressure measurement, with no return to near its initial value, could be indicative of a permanent movement or slippage of the lead.

In response to the changes in relative pressure measurements P2 or P3, correction circuitry programmed or wired into the µC 130 alters the amplitude (or energy) of the subsequently applied stimulus or stimuli to change by an amount aimed at maintaining the stimulus energy delivered to the neural tissue at a constant, efficacious level.

It is the energy content of the stimulus pulse that is adjusted in accordance with the invention when a change in the coupling efficiency has been detected. The energy content of the stimulus pulse is readily adjusted by adjusting the amplitude of the stimulus pulse. However, the energy content can also be adjusted by changing the width, or duration, of the stimulus pulse waveform, as well as the frequency with which the stimulus pulse is applied. Thus, as used herein, the term "amplitude", or "magnitude", although commonly used to signify a change in the value of a pulse, may be understood, instead, in the present context to broadly mean the "amplitude" or "magnitude" of the energy content of a stimulus pulse or a train of pulses. Thus, as used herein, a change of stimulus "amplitude" or "magnitude" of a pulse may be equivalently achieved by changing pulse amplitude, pulsewidth, frequency of the pulses or any combination of the three stimulus parameters thereof.

Figure 6:
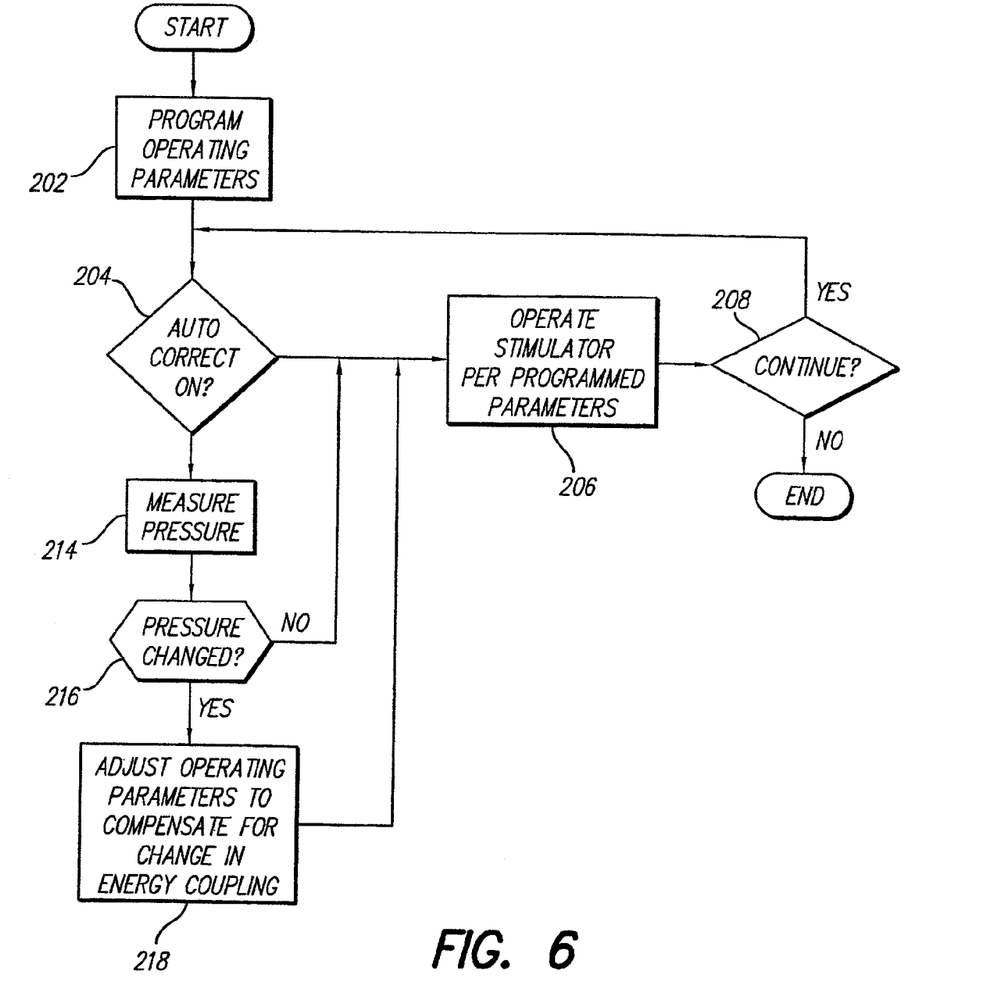
FIG. 6 is a high level flow chart that shows a method of practicing the invention in accordance with one embodiment thereof.

FIG. 6 is a high level flow chart that shows a method of practicing the invention in accordance with one embodiment thereof. As seen in FIG. 6, a first step involves programming the operating parameters (block 202) into the IPG circuitry. Such operating parameters include not only the operating regime for the neural stimulation system, e.g., stimulation pulse amplitude, pulsewidth, frequency, and electrodes, but also the parameters used by the invention to determine when a sufficient change in the sensed pressure has occurred to trigger the auto correction features of the invention.

As a preliminary matter, because various electrode types may be used in combination with different electrode configurations, it is preferred that each patient undergo a lab analysis to correlate the sensed pressure changes with a predicted adjustment to the magnitude of the adjusted stimulation in order to actually deliver an approximately constant magnitude of stimulus energy at the actual target neural tissue. For example, the correlation provides an answer to whether an increase in relative pressure corresponds to an adjustment requiring an increase or decrease in the stimulus energy. To obtain this correlation data, the patient can be instructed to make various positional changes while a test stimulus, similar to that shown in FIG. 5, is applied through a stimulating electrode and responsive pressure measurements are recorded as a function of the positional changes. In addition, it may be necessary to vary the stimulus amplitude during the assessment test to determine the just noticeable stimulation ("perception threshold") at a particular patient position and the "maximum comfortable" level of stimulation in order to interpolate and correlate the positional change with a change in stimulus energy delivered to the neural tissue. This correlation data can then be stored into memory 140 or other memory in the IPG which can then be recalled and used to analyze the indication of each sensed pressure measurement.

A more sophisticated method for correlating an event with a change in relative pressure employs the morphology of the pressure curve. A short-term event can produce a short-term relative pressure change having its own characteristic morphology such as shown by pressure waveforms P2 and P3 in FIG. 5. Pressure changes caused by different body movements may have different morphologies. If a pressure morphology can be linked to an associated corrective adjustment, when that same morphology is sensed by the IPG, the proper corrective adjustment may be applied automatically.

A specific method of implementing this linkage is to generate a correlation table ("look-up" table) which may be developed, for example, for different body movements. A short-term postural change ("an event") may occur over a time, $T_e$. The types of postural events that should be included in the catalog of short term body movements are those movements normally made during the day, e.g., sitting to lying, standing to lying, lying to standing, sitting to standing and vice versa, twisting the torso to one or the other side, running, etc. Each of these events must be characterized in the laboratory for each patient to generate a personalized look-up table that correlates the body movements/events with a characteristic pressure morphology, over a time, $T_e$. In addition, for each event characterized, there is linked a corresponding predicted adjustments (up or down) to the stimulus energy, which may be adjusted, through magnitude adjust 115, by varying pulse amplitude, pulsewidth, and pulse frequency. To obtain usable pressure morphology associated with each body movement, it is necessary that a sufficient number of pressure values are sampled with the event time, $T_e$. The IPG 12 can have automatic capability to capture pressure datapoints over a total recording time, $T_r$, which should be greater than $T_e$. These data may be uplinked to an external programmer (not shown) having processing capability or, alternatively, a computer which can be used to analyze and set the corrective stimulus adjustments. After the entire look-up table is generated, including corrective stimulus adjustments linked one-to-one to each stored characteristic pressure waveform morphology, the data table can be downloaded to the IPG to be stored in memory. In accordance with the method of the present invention, this look-up table may then be recalled by software in the IPG to make nearly instantaneous corrective adjustments to stimulus energy as a function of an identified short-term, pressure waveform morphology.

Once all the operating parameters have been programmed, a determination is made as to whether the auto correction feature of the invention has been programmed ON (block 204). If not, then the stimulator operates in accordance with its programmed operating regime without invoking the auto correction feature (block 206). Unless such programmed operating regime is turned off (block 208), this process continues.

If auto correction is turned ON (block 204), then a pressure measurement is made (block 214), either by pulsing the pressure transducer or sampling the transducer output. Once the relative pressure has been measured, then a determination is made as to whether the relative pressure has changed (block 216). If not, then the operation of the stimulator continues per its programmed parameters (block 206), and the process continues.

If a determination is made that the relative pressure measurement has changed (block 216), then the operating parameters, e.g., stimulation current amplitude, are adjusted to compensate for the change in energy coupling (block 218), and the stimulator is operated in accordance with such newly adjusted parameters (block 206). The selection of the stimulus amplitude (or energy) may be based on predetermined calculations or based on a pre-programmed lookup table as previously described. In this manner, negative feedback is provided through use of the pressure measurement to maintain the energy coupling and the energy delivered to the neural tissue at substantially a constant (or programmed) level. The set level for maintaining the energy delivered to the neural tissue may be a pre-programmed single level or it may be a preprogrammed range that is above the just noticeable stimulation ("perception threshold") and below the maximum comfortable stimulation. Stimulation energies above the maximum comfortable stimulation level will cause pain.

It is emphasized that while the present invention has been explained specifically in the context of the SCS application, the present invention can be practiced where the nerve stimulated is a peripheral as well as a spinal cord nerve. All figures except FIG. 2 apply equally to the case of stimulating peripheral nerve. FIG. 1 shows an in-line electrode array 18. In comparison, in peripheral nerve application the lead type and electrode configuration used may be different. Peripheral nerve application also differs from SCS application in that the stimulation provides different physical results. In SCS, sensory fibers are stimulated. In peripheral nerve application, motor nerves are stimulated which contract voluntary muscle such as in the arms and legs or involuntary, smooth muscle, such as those for constricting veins. The method and system of the present invention is not dependent, however, on a specific type of lead or electrode configuration used. Rather, the present invention can be applied equally effectively for the purpose of autocorrecting stimulus energy applied to peripheral nerve stimulation following a detected change in relative pressure. Thus, it is within the contemplation of the present invention to include within its scope the application where peripheral nerve is stimulated.

As described above, it is thus seen that the present invention provides a neural stimulation system wherein the output stimulus magnitude is automatically corrected or adjusted in order to compensate for coupling efficiency variations in the electrode-to-neural-tissue interface that cause more or less energy to reach the neural tissue from the electrode. Variations in the coupling efficiency are determined, in a preferred embodiment, by sensing relative changes in the measured pressure in the vicinity of the electrode-tissue interface.

As further described above, it is seen that the invention provides a method of neural stimulation that includes measuring relative pressure at or near the electrode-tissue interface, which measurements are indicative of the coupling efficiency of the electrical stimulation current to the neural tissue, and then automatically adjusting the magnitude of subsequent stimulus pulses in order to compensate for variations in the measured coupling efficiency.

While the invention herein disclosed has been described by means of specific embodiments and applications thereof, numerous modifications and variations could be made thereto by those skilled in the art without departing from the scope of the invention set forth in the claims.

What is claimed is:

1. A method of stimulating neural tissue using at least one electrode, comprising:
    measuring pressure indicative of the electrical coupling efficiency between the at least one electrode and the neural tissue;
    delivering stimulation energy through the at least one electrode to the neural tissue; and
    automatically adjusting the stimulation energy delivered through the at least one electrode to the neural tissue based on the pressure measurement.

2. The method of claim 1, wherein the pressure is measured in the vicinity of an interface between the at least one electrode and the neural tissue.

3. The method of claim 1, wherein the pressure is measured in an epidural space.

4. The method of claim 1, wherein the pressure is the relative pressure applied between the at least one electrode and the neural tissue.

5. The method of claim 1, wherein the magnitude of the stimulation energy delivered through the at least one electrode to the neural tissue is automatically adjusted based on the pressure measurement.

6. The method of claim 5, wherein the magnitude of the stimulation energy is automatically adjusted from one non-zero level to another different non-zero level.

7. The method of claim 1, wherein one or more of a pulse amplitude, pulse width, and pulse frequency of the stimulation energy delivered through the at least one electrode to the neural tissue is automatically adjusted based on the pressure measurement.

8. The method of claim 1, wherein the stimulation energy delivered through the at least one electrode to the neural tissue is automatically adjusted in order to maintain an optimal level of therapy.

9. The method of claim 8, wherein the optimal level of therapy is a predetermined therapeutic range of stimulation energy that elicits a response between a perception threshold and a discomfort threshold.

10. The method of claim 1, wherein the at least one electrode is mounted to an electrode lead.

11. The method of claim 1, wherein the automatic stimulation energy adjusting is performed in an implantable pulse generator.

12. The method of claim 1, further comprising determining a difference in the measured pressure over time, wherein the stimulation energy delivered through the at least one electrode to the neural tissue is automatically adjusted based on the determined pressure difference.

13. The method of claim 1, further comprising correlating a decrease or increase in the pressure measurement with an increase or decrease in stimulation energy delivered to the neural tissue, wherein the stimulation energy delivered through the at least one electrode to the neural tissue is automatically adjusted based on the correlation.

14. The method of claim 13, wherein the correlation step comprises:
linking each characteristic morphology caused by an event to a particular corrective adjustment for delivering a predetermined stimulation energy to the neural tissue; and
storing the linked information between each characteristic morphology to a particular corrective adjustment;
the method further comprising recalling the linked information, wherein the stimulation energy delivered through the at least one electrode to the neural tissue is automatically adjusted based on the recalled linked information.

15. The method of claim 14, wherein the event is a postural movement, and the linking step comprises measuring a pressure waveform for each postural movement while a patient makes various postural movements.

16. A neural stimulation system, comprising:
at least one electrode;
a pressure transducer configured for detecting pressure indicative of the electrical coupling efficiency between the at least one electrode and neural tissue;
analog circuitry configured for delivering stimulation energy to the at least one electrode in order to stimulate the neural tissue; and
control circuitry configured for automatically adjusting the stimulation energy delivered from the analog circuitry to the at least one electrode based on the detected pressure.

17. The neural stimulation system of claim 16, wherein the pressure transducer is configured for detecting the pressure in the vicinity of an interface between the at least one electrode and the neural tissue.

18. The neural stimulation system of claim 16, wherein the pressure transducer is configured for detecting the pressure in an epidural space.

19. The neural stimulation system of claim 16, wherein the pressure is the relative pressure applied between the at least one electrode and the neural tissue.

20. The neural stimulation system of claim 16, wherein the control circuitry is configured for automatically adjusting the magnitude of the stimulation energy delivered to the at least one electrode based on the pressure detection.

21. The neural stimulation system of claim 20, wherein the control circuitry is configured for automatically adjusting the magnitude of the stimulation energy from one non-zero level to another different non-zero level.

22. The neural stimulation system of claim 16, wherein the control circuitry is configured for automatically adjusting one or more of a pulse amplitude, pulse width, and pulse frequency of the stimulation energy delivered to the at least one electrode based on the pressure detection.

23. The neural stimulation system of claim 16, wherein the control circuitry is configured for automatically adjusting the stimulation energy delivered to the at least one electrode in order to maintain an optimal level of therapy.

24. The neural stimulation system of claim 23, wherein the optimal level of therapy is a predetermined therapeutic range of stimulation energy that elicits a response between a perception threshold and a discomfort threshold.

25. The neural stimulation system of claim 16, further comprises an electrode lead on which the at least one electrode is mounted.

26. The neural stimulation system of claim 16, further comprising an implantable pulse generator in which the analog circuitry and control circuitry are contained.

27. The neural stimulation system of claim 16, wherein the control circuitry is configured for determining a difference in the measured pressure over time, and for automatically adjusting the stimulation energy delivered to the at least one electrode based on the determined pressure difference.

28. The neural stimulation system of claim 16, further comprising memory correlating a decrease or increase in the pressure measurement with an increase or decrease in stimulation energy delivered to the neural tissue, wherein the control circuitry is configured for automatically adjusting the stimulation energy delivered to the at least one electrode based on the correlation.

29. The neural stimulation system of claim 28, wherein the memory correlates by storing information linking each characteristic morphology caused by an event to a particular corrective adjustment for delivering a predetermined stimulation energy to the neural tissue, wherein the control circuitry is configured for recalling the linked information from the memory and automatically adjusting the stimulation energy delivered to the at least one electrode based on the recalled linked information.

30. The neural stimulation system of claim 29, wherein the event is a postural movement, and the linking information comprises a pressure waveform for each of a variety of postural movements.

* * * * *